(12) United States Patent
Stevenson

(10) Patent No.: US 9,943,468 B2
(45) Date of Patent: Apr. 17, 2018

(54) CLEANSING COMPOSITIONS WITH IMPROVED DISPENSING AND SUSPENSION PROPERTIES

(71) Applicant: Conopco, Inc., Englewood Cliffs, NJ (US)

(72) Inventor: Paul Simon Stevenson, Liverpool (GB)

(73) Assignee: CONOPCO, INC., Englewood Cliffs, NJ (US)

(*) Notice: Subject to any disclaimer, the term of this patent is extended or adjusted under 35 U.S.C. 154(b) by 0 days.

(21) Appl. No.: 14/785,093

(22) PCT Filed: Apr. 4, 2014

(86) PCT No.: PCT/EP2014/056798
§ 371 (c)(1),
(2) Date: Oct. 16, 2015

(87) PCT Pub. No.: WO2014/173659
PCT Pub. Date: Oct. 30, 2014

(65) Prior Publication Data
US 2016/0081890 A1    Mar. 24, 2016

(30) Foreign Application Priority Data
Apr. 25, 2013 (EP) .................................. 13165317

(51) Int. Cl.
| A61K 8/04 | (2006.01) |
| A61Q 5/02 | (2006.01) |
| A61K 8/60 | (2006.01) |
| C11D 1/66 | (2006.01) |
| C11D 1/83 | (2006.01) |
| C11D 17/00 | (2006.01) |
| A61K 8/11 | (2006.01) |
| A61K 8/46 | (2006.01) |
| A61Q 5/00 | (2006.01) |
| C11D 1/28 | (2006.01) |

(52) U.S. Cl.
CPC .............. *A61K 8/044* (2013.01); *A61K 8/11* (2013.01); *A61K 8/463* (2013.01); *A61K 8/602* (2013.01); *A61Q 5/02* (2013.01); *C11D 1/28* (2013.01); *C11D 1/662* (2013.01); *C11D 1/83* (2013.01); *C11D 17/0013* (2013.01); *C11D 17/0039* (2013.01); *A61K 2800/56* (2013.01); *A61Q 5/006* (2013.01)

(58) Field of Classification Search
CPC .... A61K 8/602; A61K 2800/56; A61K 8/044; A61K 8/11; A61K 8/463; A61Q 17/005; A61Q 5/006; A61Q 5/02; C11D 1/00; C11D 1/94; C11D 17/0013; C11D 17/0039; C11D 1/28; C11D 1/662; C11D 1/83
See application file for complete search history.

(56) References Cited

U.S. PATENT DOCUMENTS

| 2,800,457 | A | 7/1957 | Green et al. |
| 3,516,941 | A | 6/1970 | Matson |
| 4,145,184 | A | 3/1979 | Brain |
| 4,318,901 | A | 3/1982 | Ishida et al. |
| 4,406,816 | A | 9/1983 | Sliwka |
| 4,902,512 | A | 2/1990 | Ishigami et al. |
| 5,112,688 | A | 5/1992 | Michael |
| 5,417,879 | A | 5/1995 | Hall et al. |
| 5,635,464 | A * | 6/1997 | Nakamura ............... C11D 1/29 510/218 |
| 6,336,977 | B1 | 1/2002 | Menke et al. |
| 7,939,489 | B2 | 5/2011 | Shah et al. |
| 8,524,650 | B2 | 9/2013 | Denutte et al. |
| 2007/0138671 | A1 * | 6/2007 | Anastasiou ............. B01J 13/14 264/4.1 |
| 2007/0138674 | A1 | 6/2007 | Anastasiou et al. |
| 2008/0213194 | A1 * | 9/2008 | DeSanto ................ A01N 43/16 424/49 |
| 2010/0234262 | A1 * | 9/2010 | Smith ..................... C11D 3/046 510/161 |
| 2011/0002984 | A1 * | 1/2011 | Atkin .................... A61K 9/5063 424/451 |
| 2011/0152146 | A1 * | 6/2011 | Denutte .................. A61K 8/11 510/119 |
| 2012/0022241 | A1 * | 1/2012 | Gross ..................... A01N 25/30 536/17.9 |
| 2013/0331466 | A1 * | 12/2013 | Gross ..................... C07H 15/04 514/777 |

FOREIGN PATENT DOCUMENTS

| CN | 101007259 | 8/2007 |
| CN | 102695491 | 9/2012 |
| DE | 19628454 | 1/1998 |

(Continued)

OTHER PUBLICATIONS

Nguyen et al (International Journal of Molecular Sciences, Feb. 2011, vol. 12, pp. 1232-1244).*
Search Report in EP13165317, dated Sep. 19, 2013 (NPL 1).
Search Report in PCTEP2014056798, dated Jul. 24, 2014, pp. 1-4, WO (NPL 2).
Written Opinion in EP13165317, dated Sep. 29, 2013 (NPL 3).
Written Opinion in PCTEP2014056798, dated Jul. 24, 2014, pp. 1-5, WO (NPL 4).

*Primary Examiner* — Mark V Stevens
(74) *Attorney, Agent, or Firm* — Foley & Lardner LLP

(57) ABSTRACT

A fluid cleaning composition comprising: (a) a surfactant combination comprising: (i) a synthetic surfactant; and (ii) a glycolipid biosurfactant which is present at a level in the range 10-9 wt % of the total surfactant in said surfactant combination, and (b) a benefit agent suspended in said fluid cleaning composition characterized in that the benefit agent comprises an encapsulate.

22 Claims, 2 Drawing Sheets

(56) References Cited

FOREIGN PATENT DOCUMENTS

| | | | | |
|---|---|---|---|---|
| EP | 0550279 | 5/1996 | | |
| EP | 1445302 | 8/2004 | | |
| EP | 1964546 | 9/2008 | | |
| EP | 2055314 | 5/2009 | | |
| EP | 2277860 | 1/2011 | | |
| EP | 2410039 A1 * | 1/2012 | ........... | C11D 3/0036 |
| GB | 2006709 | 5/1979 | | |
| GB | 2062570 | 5/1981 | | |
| JP | 63077535 | 4/1988 | | |
| JP | 2001518969 A | 10/2001 | | |
| JP | 2013513720 A | 4/2013 | | |
| KR | 2009117081 | 11/2009 | | |
| WO | WO9943334 | 9/1999 | | |
| WO | WO2003006146 | 1/2003 | | |
| WO | WO2008013899 | 1/2008 | | |
| WO | WO2010129285 | 11/2010 | | |
| WO | WO2011075551 | 6/2011 | | |
| WO | WO 2011120776 A1 * | 10/2011 | ............... | A61K 8/44 |
| WO | WO2012077120 | 6/2012 | | |
| WO | WO2013026656 | 2/2013 | | |
| WO | WO20130266657 | 2/2013 | | |
| WO | WO2013043857 | 3/2013 | | |

\* cited by examiner

CLEANSING COMPOSITIONS WITH IMPROVED DISPENSING AND SUSPENSION PROPERTIES

This invention relates to cleaning fluid compositions comprising benefit agents which also have improved dispensing properties. The compositions are in particular, but not exclusively, for use in aqueous based treatments such as personal bathing, washing of fabrics and dishes.

Fluid compositions may comprise benefit agents delivering advanced benefits however these compositions require structuring or thickening ingredients to prevent the benefit agents from migrating under gravity.

An object of the invention is to provide a composition for personal bathing and/or washing of dishes and/or fabrics which comprise benefit agents and also with improved dispensing properties.

According to the present invention there is provided a fluid cleaning composition comprising:
 (a) a surfactant combination comprising:
  (i) a synthetic surfactant; and
  (ii) a glycolipid biosurfactant which is present at a level in the range 10-95 wt % of the total surfactant in said surfactant combination, and
 (b) a benefit agent suspended in said fluid cleaning composition characterised in that the benefit agent comprises an encapsulate.

The substrate is preferably a fabric surface or a hard surface (such as a work surface or cutlery or crockery) or human skin or hair or teeth.

The invention is particularly advantageous in that the glycolipid biosurfactant offers rheological modifying properties for compositions comprising suspending agents, whereby benefit agents are suspended without the need for additional suspending technologies such as structurants, but at the same time shear-thinning properties allow for ease of dispensing via smaller apertures for accurate dispensing/dosing.

Throughout this specification where "%" is used, it is intended to mean % by weight (wt. %).

Preferably the glycolipid comprises a rhamnolipid, however other glycolipids may be used such as sophorolipids or any combination thereof.

Preferably the composition comprises an ionic salt. The salt preferably comprises any organic or inorganic cation, including without limitation cations of alkali metals Cs, Na, K, Ca, Mg etc., with anions including halide anions, more preferably Cl. Other preferred salts comprise organic cations e.g. amides ($-^+$NH—R) or ammonium cations or substituted forms thereof e.g. triethylammonium. Anions for organic cations may comprise any akyl, aryl, arylalkyl moiety which may be short, medium, long, branched, cyclic or linear.

Preferably the composition comprises from 0.01-5 wt % by weight of the salt. In the case of NaCl, preferably the level is in the range 0.5-2 wt. %

Preferably the glycolipid is present at 25%-75% by weight of the surfactant combination.

The surfactant combination preferably comprises a synthetic anionic surfactant. 'Anionic surfactants' are defined herein as amphiphilic molecules comprising one or more functional groups that exhibit a net anionic charge when in aqueous solution at the normal wash pH of between 4 and 11.

Preferably the alkali metal salts of organic sulphur reaction products having in their molecular structure an alkyl moiety containing from about 6 to 24 carbon atoms, more greater than 12 carbon atoms and preferably also a moiety selected from the group consisting of sulphonic and sulphuric acid ester moieties. Additionally or alternatively, the anionic surfactant preferably has low levels of ethoxylation, preferably comprising 1-12 ethylene oxide units per molecule, more preferably 1-3 and even more preferably 1. The units of ethylene oxide may be an average.

Providing the formulation scientist with the freedom to use longer carbon chain lengths and/or lower levels of ethoxylation is greatly beneficial, not least on cost grounds. However these factors increase calcium intolerance and so such surfactants are advantageous selections for the present invention.

Preferred anionic surfactants include primary alkyl sulphates (PAS) e.g. sodium lauryl sulphate (SLS) and e.g. alkyl ether sulphate such as sodium lauryl ether sulphate (SLES), soaps, fatty acid ester sulphonates, fatty acid sulphates or sulphonates; alkyl benzene sulphonates (LAS), sulphosuccinate esters, olefin sulphonates, paraffin sulphonates and organic phosphates; fatty alcohol sulphates; alkyl phenol ether sulphate; fatty acyl isethionate products which products comprise fatty acyl isethionate and free fatty acid and/or fatty acid salt; alkyl sulphonates such as sodium alkane sulphonate. Preferred anionic surfactants are the alkali (ammonium or triethylammonium for example) and alkaline earth metal salts of the above. The source oil/alcohol can be plant or animal derived for example coconut or palm or tallow etc.

The surfactant combination is present in the fabric or hard surface washing compositions at a level of from 3 to 85% by weight, preferably from 3 to 60% by weight, more preferably from 3 to 40% by weight, most preferably from 3 to 35% by weight.

The surfactant combination is present in personal (human skin and hair) wash compositions at a level of 5 to 60%, preferably 10 to 40% surfactant, while cosmetic compositions need not comprise any surfactant, but preferably comprise 1% to 30% by wt., more preferably 1 to 15% by wt. surfactant.

The invention is particularly advantageous in suspending larger components in fluid compositions as compared with more expensive rheology modifiers.

Accordingly, it is preferred that the benefit agent is macroscopic i.e. greater than or equal to 3 micrometers in diameter.

The encapsulate preferably comprises a shell or capsule surrounding a core, wherein the core comprises the benefit agent.

Preferably the encapsulate comprises microcapsules. Preferably the encapsulate comprises shear/pressure-sensitive action encapsulates, whereby the sensorial benefit agent contained within is released in response to mechanical force (e.g., friction, pressure, shear stress) on the encapsulate. Urea-formaldehyde and melamine-formaldehyde microcapsules may be used to provide the necessary friction or pressure based release mechanism.

Additionally or alternatively, the encapsulates may also be of diffusive action, wherein sensorial benefit agent contained within is also released by diffusion through the outer wall of the encapsulate.

Commercially available melamine formaldehyde based, friction release encapsulates are the Aroma Ball Type 1 and Aroma Ball S-series encapsulates ex. Polychrome, Korea.

Preferably the shell is a melamine formaldehyde shell. The encapsulate shell is preferably comprised of materials including but not limited to polyurethane, polyamide, polyolefin, polysaccaharide, protein, silicone, lipid, modified cellulose, gums, polyacrylate, polyphosphate, polystyrene, polyesters or combinations of these materials. Other encapsulating material which may be used effectively in the present invention, such as polymethylmethacrylate. Preferred encapsulating polymers include those formed from melamine formaldehyde or urea formaldehyde condensates, as well as similar types of aminoplasts. Most preferably the shell comprises melamine formaldehyde.

Additionally, microcapsules made via the simple or complex coacervation of gelatin are suitable for use in compositions of the invention.

A representative process used for aminoplast encapsulation is disclosed in U.S. Pat. No. 3,516,941 though it is recognised that many variations with regard to materials and process steps are possible. A representative process used for gelatin encapsulation is disclosed in U.S. Pat. No. 2,800,457 though it is recognized that many variations with regard to materials and process steps are possible. Both of these processes are discussed in the context of fragrance encapsulation for use in consumer products in U.S. Pat. Nos. 4,145,184 and 5,112,688 respectively.

Encapsulation can provide pore vacancies or interstitial openings depending on the encapsulation techniques employed.

Fragrance capsules known in the art and suitable for use in the present invention comprise a wall or shell comprising a three-dimensional cross-linked network of an aminoplast resin, more specifically a substituted or un-substituted acrylic acid polymer or co-polymer cross-linked with a urea-formaldehyde pre-condensate or a melamine-formaldehyde pre-condensate.

Microcapsule formation using mechanisms similar to the foregoing mechanism, using (i) melamine-formaldehyde or urea-formaldehyde pre-condensates and (ii) polymers containing substituted vinyl monomeric units having proton-donating functional group moieties (e.g. sulfonic acid groups or carboxylic acid anhydride groups) bonded thereto is disclosed in U.S. Pat. No. 4,406,816 (2-acrylamido-2-methyl-propane sulfonic acid groups), published Patent Application GB 2,062,570 A (styrene sulfonic acid groups) and published Patent Application GB 2,006,709 A (carboxylic acid anhydride groups).

The encapsulate may further comprise a carrier oil in the core. The carrier oils are hydrophobic materials that are miscible in the volatile benefit agent materials used in the present invention. Suitable oils are those having reasonable affinity for the benefit agent. Where the benefit agent is a perfume, suitable materials include, but are not limited to triglyceride oil, mono and diglycerides, mineral oil, silicone oil, diethyl phthalate, polyalpha olefins, castor oil and isopropyl myristate. Preferably, the oil is a triglyceride oil, most preferably a capric/caprylic triglyceride oil.

Particle size and average diameter of the capsules can vary from about 10 nanometers to about 1000 microns, preferably from about 50 nanometers to about 100 microns, more preferably from about 2 to about 40 microns, even more preferably from about 4 to 15 microns. A particularly preferred range is from about 5 to 10 microns, for example 6 to 7 microns. The capsule distribution can be narrow, broad or multimodal. Multimodal distributions may be composed of different types of capsule chemistries.

The shell may further comprise a deposition aid, which is preferably covalently attached.

A preferred deposition aid is a polysaccharide. The polysaccharide preferably has a β-1,4-linked backbone.

Preferably the polysaccharide is a cellulose, a cellulose derivative, or another β-1,4-linked polysaccharide having an affinity for cellulose, such as polymannan, polyglucan, polyglucomannan, polyxyloglucan and polygalactomannan or a mixture thereof. More preferably, the polysaccharide is selected from the group consisting of polyxyloglucan and polygalactomannan.

Highly preferred polysaccharides are selected from locust bean gum, tamarind gum, xyloglucan, non-ionic guar gum, cationic starch and mixtures thereof. Most preferably, the deposition aid is locust bean gum.

Preferably, the polysaccharide backbone has only β-1,4 linkages. Optionally, the polysaccharide has linkages in addition to the β-1,4 linkages, such as β-1,3 linkages. Thus, optionally some other linkages are present. Polysaccharide backbones which include some material which is not a saccharide ring are also within the ambit of the present invention (whether terminal or within the polysaccharide chain).

The polysaccharide may be straight or branched. Many naturally occurring polysaccharides have at least some degree of branching, or at any rate at least some saccharide rings are in the form of pendant side groups (which are therefore not in themselves counted in determining the degree of substitution) on a main polysaccharide backbone.

Preferably, the polysaccharide is present at levels of between 0.1% to 10% w/w by weight of the total amount of the particle.

The deposition aid, which is preferably a polysaccharide, is attached to the particle by means of a covalent bond, entanglement or strong adsorption, preferably by a covalent bond or entanglement and most preferably by means of a covalent bond. By entanglement as used herein is meant that the deposition aid is adsorbed onto the particle as the polymerisation proceeds and the particle grows in size, part of the adsorbed deposition aid becomes buried within the interior of the particle. Hence at the end of the polymerisation, part of the deposition aid is entrapped and bound in the polymer matrix of the particle, whilst the remainder is free to extend into the aqueous phase.

By strong adsorption as used herein is meant strong adsorption of the deposition aid to the surface of the particle; such adsorption can, for example, occur due to hydrogen bonding, Van Der Waals or electrostatic attraction between the deposition aid and the particle.

The deposition aid is thus mainly attached to the particle surface and is not, to any significant extent, distributed throughout the internal bulk of the particle. This is distinct from graft copolymers in which e.g. a polysaccharide may be grafted along the length of a polymer chain. A particle which is formed from a graft copolymer would, therefore, contain polysaccharide throughout the internal bulk of the particle as well as on the particle surface and the present invention is not intended to cover such a particle. Thus the particle which is produced when using a polysaccharide as the deposition aid according to the process of the invention can be thought of as a "hairy particle", which is different from a graft copolymer. This feature of the invention provides significant cost reduction opportunities for the manufacturer as much less deposition aid is required to achieve the same level of activity as systems which utilise polysaccharide copolymers.

The deposition aid is present in the outermost portion of the shell, which is made of melamine formaldehyde polymer having a thickness of from 5 to 20 nm.

Polyesters of terephthalic and other aromatic dicarboxylic acids having soil release properties, in particular, the so-called PET/POET (polyethylene terephthalate/polyoxyethylene terephthalate) and PET/PEG (polyethylene terephthalate/polyethylene glycol) polyesters may be employed as deposition aids.

The polymer must have at least one mole free OH group per mole polymer, to allow covalent binding to the reactive dye(s). Most preferably the polymer comprises at least two free OH groups. Preferably the OH groups are the terminal groups of the polymer.

Preferably, the oxyalkyleneoxy [—O(CH$_2$)$_t$O—] is selected from: oxy-1,2-propyleneoxy [—OCH$_2$CH(Me)O—]; oxy-1,3-propyleneoxy [O—CH$_2$CH$_2$CH$_2$O—]; and, oxy-1,2-ethyleneoxy [—OCH$_2$CH$_2$O—] (t is an interger). As is evident one or more of the CH$_2$ groups of the oxyalkyleneoxy may be substituted by C1 to C4 alkyl group(s).

The polyoxyalkyleneoxy facilitates water solubility of the polymer. Preferably, the polyoxyalkyleneoxy [—O(CH$_2$)$_w$—]$_s$O— is selected from: polyoxy-1,2-propyleneoxy [—O(CH$_2$CH(Me)-]$_s$O—; polyoxy-1,3-propyleneoxy [O—CH$_2$CH$_2$CH$_2$—]$_s$O—; and, polyoxy-1,2-ethyleneoxy [O—CH$_2$CH$_2$—]$_s$O—; The polyoxyalkyleneoxy may be a mixture of different oxyalkyleneoxy. Different polyoxyalkyleneoxy types may present in the polymer. (s and w are intergers).

Preferably the phenyl dicarboxylate is a 1,4-phenyl dicarboxylate. Preferably the phenyl dicarboxylate is of the form: —OC(O)C$_6$H$_4$C(O)O—.

Examples of preferred polymers are a PET/POET (Polyethylene terephthalate/polyoxyethylene terephthalate), PEG/POET (Polyethyleneglycol/polyoxyethylene terephthalate) or PET/PEG (Polyethylene terephthalate/Polyethyleneglycol) polymer. Most preferable a PET/POET.

The structure of a preferred polymer is found below.

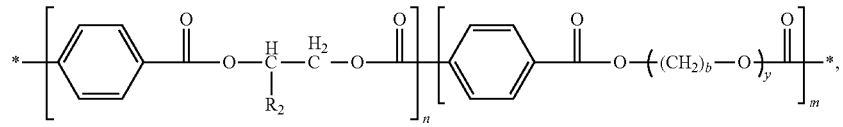

wherein

R$_2$ is selected from H or CH$_3$, preferably H;

b is 2 or 3, preferably 2;

y is 2 to 100, preferably 5 to 50;

n and m are independently 1 to 100, preferably 2 to 30; and, the terminal (end) groups of the polymer are (CH$_2$)$_b$OH.

The polymers may be synthesised by a variety of routes, for example an esterification reaction of dimethyl terephthalate with ethyleneglycol and polyethyleneglycol, this reaction is discussed in Polymer Bulletin 28, 451-458 (1992). Another example would be the direct esterification of terephthalic acid with ethylene glycol and/or propylene glycol and polypropylene glycol. A further example would be a transesterification of a polyethyleneterephthalate with a polyethyleneglycol or polypropylene gycol.

It is preferred that the number average molecular weight of the polymer is in the range from 1000 to 50,000, preferably the average molecular weight of the polymer is in the range of from 1000 to 15000, more preferably from 2000 to 10000.

Preferably the encapsulated benefit agent comprises a skin benefit agent or an olfactory benefit agent and/or may be a volatile benefit agent. Sensorial benefit agents may also have benefits for hair and/or hard surfaces and/or fabrics.

Suitable volatile benefit agents include but are not limited to perfumes, insect repellents, essential oils, sensates such as menthol and aromatherapy actives, preferably perfumes. Mixtures of volatile benefit agents may be used.

The total amount of benefit agent is preferably from 0.01 to 10% by weight, more preferably from 0.05 to 5% by weight, even more preferably from 0.1 to 4.0%, most preferably from 0.15 to 4.0% by weight, based on the total weight of the composition.

A preferred benefit agent is a perfume. The compositions of the invention also comprise an unconfined (also called non-encapsulated) volatile benefit agent. Where the volatile benefit agent is a perfume, the perfumes described below are suitable for use as the encapsulated volatile benefit agent and also as the unconfined perfume component.

Any suitable perfume or mixture of perfumes may be used. Useful components of the perfume include materials of both natural and synthetic origin. They include single compounds and mixtures. Specific examples of such components may be found in the current literature, e.g., in Fenaroli's Handbook of Flavor Ingredients, 1975, CRC Press; Synthetic Food Adjuncts, 1947 by M. B. Jacobs, edited by Van Nostrand; or Perfume and Flavor Chemicals by S. Arctander 1969, Montclair, N.J. (USA). These substances are well known to the person skilled in the art of perfuming, flavouring, and/or aromatizing consumer products, i.e., of imparting an odour and/or a flavour or taste to a consumer product traditionally perfumed or flavoured, or of modifying the odour and/or taste of said consumer product.

By perfume in this context is not only meant a fully formulated product fragrance, but also selected components of that fragrance, particularly those which are prone to loss, such as the so-called 'top notes'.

Top notes are defined by Poucher (Journal of the Society of Cosmetic Chemists 6(2):80 [1955]). Examples of well known top-notes include citrus oils, linalool, linalyl acetate, lavender, dihydromyrcenol, rose oxide and cis-3-hexanol. Top notes typically comprise 15-25% wt of a perfume composition and in those embodiments of the invention which contain an increased level of top-notes it is envisaged at that least 20% wt would be present within the encapsulate.

Some or all of the perfume or pro-fragrance may be encapsulated, typical perfume components which it is advantageous to encapsulate, include those with a relatively low boiling point, preferably those with a boiling point of less than 300, preferably 100-250 Celsius and pro-fragrances which can produce such components.

It is also advantageous to encapsulate perfume components which have a low C log P (ie. those which will be partitioned into water), preferably with a C log P of less than 3.0. These materials, of relatively low boiling point and relatively low C log P have been called the "delayed blooming" perfume ingredients and include the following materials:

Allyl Caproate, Amyl Acetate, Amyl Propionate, Anisic Aldehyde, Anisole, Benzaldehyde, Benzyl Acetate, Benzyl Acetone, Benzyl Alcohol, Benzyl Formate, Benzyl Iso Valerate, Benzyl Propionate, Beta Gamma Hexenol, Camphor Gum, Laevo-Carvone, d-Carvone, Cinnamic Alcohol, Cinamyl Formate, Cis-Jasmone, cis-3-Hexenyl Acetate, Cuminic Alcohol, Cyclal C, Dimethyl Benzyl Carbinol, Dimethyl Benzyl Carbinol Acetate, Ethyl Acetate, Ethyl Aceto Acetate, Ethyl Amyl Ketone, Ethyl Benzoate, Ethyl Butyrate, Ethyl Hexyl Ketone, Ethyl Phenyl Acetate, Eucalyptol, Eugenol, Fenchyl Acetate, Flor Acetate (tricyclo Decenyl Acetate), Frutene (tricycico Decenyl Propionate), Geraniol, Hexenol, Hexenyl Acetate, Hexyl Acetate, Hexyl Formate, Hydratropic Alcohol, Hydroxycitronellal, Indone, Isoamyl Alcohol, Iso Menthone, Isopulegyl Acetate, Isoquinolone, Ligustral, Linalool, Linalool Oxide, Linalyl Formate, Menthone, Menthyl Acetphenone, Methyl Amyl Ketone, Methyl Anthranilate, Methyl Benzoate, Methyl Benyl Acetate, Methyl Eugenol, Methyl Heptenone, Methyl Heptine Carbonate, Methyl Heptyl Ketone, Methyl Hexyl Ketone, Methyl Phenyl Carbinyl Acetate, Methyl Salicylate, Methyl-N-Methyl Anthranilate, Nerol, Octalactone, Octyl Alcohol, p-Cresol, p-Cresol Methyl Ether, p-Methoxy Acetophenone, p-Methyl Acetophenone, Phenoxy Ethanol, Phenyl Acetaldehyde, Phenyl Ethyl Acetate, Phenyl Ethyl Alcohol, Phenyl Ethyl Dimethyl Carbinol, Prenyl Acetate, Propyl Bornate, Pulegone, Rose Oxide, Safrole, 4-Terpinenol, Alpha-Terpinenol, and/or Viridine.

Where non-encapsulated or 'free' perfume ingredients are used, preferred are those hydrophobic perfume components with a C log P above 3. As used herein, the term "C log P" means the calculated logarithm to base 10 of the octanol/water partition coefficient (P). The octanol/water partition coefficient of a perfume raw material (PRM) is the ratio between its equilibrium concentrations in octanol and water. Given that this measure is a ratio of the equilibrium concentration of a PRM in a non-polar solvent (octanol) with its concentration in a polar solvent (water), C log P is also a measure of the hydrophobicity of a material—the higher the C log P value, the more hydrophobic the material. C log P values can be readily calculated from a program called "C LOG P" which is available from Daylight Chemical Information Systems Inc., Irvine Calif., USA. Octanol/water partition coefficients are described in more detail in U.S. Pat. No. 5,578,563.

Perfume components with a C log P above 3 comprise: Iso E super, citronellol, Ethyl cinnamate, Bangalol, 2,4,6-Trimethylbenzaldehyde, Hexyl cinnamic aldehyde, 2,6-Dimethyl-2-heptanol, Diisobutylcarbinol, Ethyl salicylate, Phenethyl isobutyrate, Ethyl hexyl ketone, Propyl amyl ketone, Dibutyl ketone, Heptyl methyl ketone, 4,5-Dihydrotoluene, Caprylic aldehyde, Citral, Geranial, Isopropyl benzoate, Cyclohexanepropionic acid, Campholene aldehyde, Caprylic acid, Caprylic alcohol, Cuminaldehyde, 1-Ethyl-4-nitrobenzene, Heptyl formate, 4-Isopropylphenol, 2-Isopropylphenol, 3-Isopropylphenol, Allyl disulfide, 4-Methyl-1-phenyl-2-pentanone, 2-Propylfuran, Allyl caproate, Styrene, Isoeugenyl methyl ether, Indonaphthene, Diethyl suberate, L-Menthone, Menthone racemic, p-Cresyl isobutyrate, Butyl butyrate, Ethyl hexanoate, Propyl valerate, n-Pentyl propanoate, Hexyl acetate, Methyl heptanoate, trans-3,3,5-Trimethylcyclohexanol, 3,3,5-Trimethylcyclohexanol, Ethyl p-anisate, 2-Ethyl-1-hexanol, Benzyl isobutyrate, 2,5-Dimethylthiophene, Isobutyl 2-butenoate, Caprylnitrile, gamma-Nonalactone, Nerol, trans-Geraniol, 1-Vinylheptanol, Eucalyptol, 4-Terpinenol, Dihydrocarveol, Ethyl 2-methoxybenzoate, Ethyl cyclohexanecarboxylate, 2-Ethylhexanal, Ethyl amyl carbinol, 2-Octanol, 2-Octanol, Ethyl methylphenylglycidate, Diisobutyl ketone, Coumarone, Propyl isovalerate, Isobutyl butanoate, Isopentyl propanoate, 2-Ethylbutyl acetate, 6-Methyl-tetrahydroquinoline, Eugenyl methyl ether, Ethyl dihydrocinnamate, 3,5-Dimethoxytoluene, Toluene, Ethyl benzoate, n-Butyrophenone, alpha-Terpineol, Methyl 2-methylbenzoate, Methyl 4-methylbenzoate, Methyl 3, methylbenzoate, sec. Butyl n-butyrate, 1,4-Cineole, Fenchyl alcohol, Pinanol, cis-2-Pinanol, 2,4, Dimethylacetophenone, Isoeugenol, Safrole, Methyl 2-octynoate, o-Methylanisole, p-Cresyl methyl ether, Ethyl anthranilate, Linalool, Phenyl butyrate, Ethylene glycol dibutyrate, Diethyl phthalate, Phenyl mercaptan, Cumic alcohol, m-Toluquinoline, 6-Methylquinoline, Lepidine, 2-Ethylbenzaldehyde, 4-Ethylbenzaldehyde, o-Ethylphenol, p-Ethylphenol, m-Ethylphenol, (+)-Pulegone, 2,4-Dimethylbenzaldehyde, Isoxylaldehyde, Ethyl sorbate, Benzyl propionate, 1,3-Dimethylbutyl acetate, Isobutyl isobutanoate, 2,6-Xylenol, 2,4-Xylenol, 2,5-Xylenol, 3,5-Xylenol, Methyl cinnamate, Hexyl methyl ether, Benzyl ethyl ether, Methyl salicylate, Butyl propyl ketone, Ethyl amyl ketone, Hexyl methyl ketone, 2,3-Xylenol, 3,4, Xylenol, Cyclopentadenanolide and Phenyl ethyl 2 phenylacetate 2.

In the compositions of the present invention it is envisaged that there will be four or more, preferably five or more, more preferably six or more or even seven or more different perfume components from the list given of delayed blooming perfumes given above and/or the list of perfume components with a C log P above 3 present in the perfume.

The benefit agent may also provide insect repellence. In chemical terms, most repellent actives belong to one of four groups: amides, alcohols, esters or ethers. Those suitable for use in the present invention are liquids or solids with a relatively low melting point and a boiling point above 150° C., preferably liquids. They evaporate slowly at room temperature.

Advantageously the insect repellent is related to perfume species (most preferably the component falls into both classes). The most commonly used insect repellents include: DEET (N,N-diethyl-m-toluamide), essential oil of the lemon eucalyptus (*Corymbia citriodora*) and its active compound p-menthane-3,8-diol (PMD), Icaridin, also known as Picaridin, D-Limonene, Bayrepel, and KBR 3023, Nepetalactone, also known as "catnip oil", Citronella oil, Permethrin, Neem oil and Bog Myrtle.

Preferred insect repellents derived from natural sources include: *Achillea alpina*, alpha-terpinene, Basil oil (*Ocimum basilicum*), *Callicarpa americana* (Beautyberry), Camphor, Carvacrol, Castor oil (*Ricinus communis*), Catnip oil (*Nepeta* species), Cedar oil (*Cedrus atlantica*), Celery extract (*Apium graveolens*), Cinnamon (*Cinnamomum Zeylanicum*, leaf oil), Citronella oil (*Cymbopogon fleusus*), Clove oil (*Eugenic caryophyllata*), Eucalyptus oil (70%+ eucalyptol, also known as cineol), Fennel oil (*Foeniculum vulgare*), Garlic Oil (*Allium sativum*), Geranium oil (also known as *Pelargonium graveolens*), Lavender oil (*Lavandula officinalis*), Lemon eucalyptus (*Corymbia citriodora*) essential oil and its active ingredient p-menthane-3,8-diol (PMD), Lemongrass oil (*Cymbopogon flexuosus*), Marigolds (*Tagetes* species), Marjoram (*Tetranychus urticae* and *Eutetranychus orientalis*), Neem oil (*Azadirachta indica*), Oleic acid, Peppermint (*Mentha×piperita*), Pennyroyal (*Mentha pulegium*), Pyrethrum (from *Chrysanthemum* species, particularly *C. cinerariifolium* and *C. coccineum*), Rosemary oil (*Rosmarinus officinalis*), Spanish Flag *Lantana camara* (*Helopeltis theivora*), *Solanum villosum* berry juice, Tea tree oil (*Melaleuca alternifolia*) and Thyme (*Thymus* species) and mixtures thereof.

Preferred encapsulated insect repellents are mosquito repellents available from Celessence, Rochester, England. Celessence Repel, containing the active ingredient Saltidin™ and Celessence Repel Natural, containing the active Citrepel™ 75. Saltidin is a man made molecule developed originally by the Bayer Corporation. Citrepel is produced from eucalyptus oils and is high in p-menthane-3,8-diol (PMD). A preferred non-encapsulated repellent is Citriodiol™ supplied by Citrefine.

Preferably the benefit agent comprises so-called 'aromatherapy' materials. These include components of essential oils such as Clary Sage, Eucalyptus, Geranium, Lavender, Mace Extract, Neroli, Nutmeg, Spearmint, Sweet Violet Leaf and Valerian.

Other benefit agents for use in this invention are meant to include but not be limited to moisturizers and/or emollients for skin and/or hair such as mineral oil, petrolatum, silicone oil such as dimethyl polysiloxane, lauryl and myristyl lactate. Emollient/oil generally will comprise, if present, 1% to 20% of the composition.

Benefit agents suitable for hair include anti-dandruff actives, for example zinc salts eg. zinc pyrithione ZnPTO, zinc sulphate and hydrates thereof; octopirox (piroctone olamine), azole antimicrobials (eg. climbazole) selenium sulphide and any combination thereof.

Preferably the level of anti-dandruff within the total composition is 0.1-5%.

Other benefit agents suitable for hair include silicones, such as polyalkyl siloxanes, polyaryl siloxanes, polyalkylaryl siloxanes, polyether siloxane copolymer and mixtures thereof; amino silicones, high molecular weight silicone gums and/or crosslinked silicone elastomers.

Preferably the silicone is present from about 0.01 to about 10 wt % of the total composition.

Other benefit agents comprise cationic polymers for conditioning hair.

A particularly suitable type of cationic polysaccharide polymer that can be used is a cationic guar gum derivative, such as guar hydroxypropyltrimonium chloride (commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic conditioning polymer is selected from cationic cellulose and cationic guar derivatives. Particularly preferred cationic polymers are JAGUAR C13S, JAGUAR C15, JAGUAR C17 and JAGUAR C16 and JAGUAR C162.

The cationic conditioning polymer will generally be present in compositions of the invention at levels of from 0.01 to 5, preferably from 0.05 to 1, more preferably from 0.08 to 0.5 percent by weight of the composition.

When cationic conditioning polymer is present in a shampoo composition according to the invention, it is preferred if the copolymer is present as emulsion particles with a mean diameter ($D_{3,2}$ as measured by light scattering using a Malvern particle sizer) of 2 micrometers or less.

Shampoo compositions of the invention are preferably aqueous, i.e. they have water or an aqueous solution or a lyotropic liquid crystalline phase as their major component.

Suitably, the composition will comprise from 50 to 98%, preferably from 60 to 90% water by weight based on the total weight of the composition.

The composition is especially useful for washing in water with a high water hardness, preferably of greater than 5° FH preferably greater than 40° FH, more preferably greater than 90° FH.

The compositions of the invention are preferably unbuilt.

The compositions of the invention may comprise other ingredients as described hereinbelow.

Vegetable oils: Arachis oil, cannola oil, castor oil, cocoa butter, coconut oil, corn oil, cotton seed oil, olive oil, palm kernel oil, rapeseed oil, safflower seed oil, sesame seed oil and soybean oil.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate.

Animal Fats: Acytylatelte lanolin alcohols, lanolin, lard, mink oil and tallow.

Fatty acids and alcohols: Behenic acid, palmitic acid, stearic acid, behenyl alcohol, cetyl alcohol, eicosanyl alcohol and isocetyl alcohol.

Benefit agents in hand washing and fabric cleaning compositions which are particularly suitable for suspending are opacifiers and visual cues, either with or without functional ingredients embedded therein and other ingredients, antimicrobials. Hand washing and fabric cleaning compositions further comprise polyester substantive soil release polymers, hydrotropes, opacifiers, colorants, other enzymes, further surfactants such as nonionic, cationic and or amphoteric surfactants, softeners, polymers for anti redeposition of soil, bleach, bleach activators and bleach catalysts, antioxidants, pH control agents and buffers, thickeners, external structurants for rheology modification, visual cues known to those skilled in the art.

The composition is preferably a liquid or gel.

The invention will be further described with reference to the following non-limiting examples in which.

PROTOCOL FOR MAKING BIOSURFACTANT SHAMPOO ACCORDING TO THE INVENTION

1. Add required SLES 1EO (28% active) to a beaker
2. Add the required biosurfactant (0%, 25%, 50% and 75% replacement of the total SLES surfactant) while mixing.
3. Add de-min water (keeping 10% of the total water to rinse in the deposition aid polymer/perfume mixture).
4. Add the Carbopol 980 (4% slurry) and leave to mix for at least 30 minutes to ensure thorough mixing.
5. Mix the Jaguar C14S and perfume together in a separate beaker, then add to the main batch. Use the water left to wash the content of the beaker into main batch. Leave the shampoo to mix for 20 minutes to allow thorough mixing 6. Add the silicone and mix for 10 minutes.
7. Add the CAPB slowly and leave to mix for 10 minutes.
8. Add Glydant preservative
9. Measure the pH of the mixture. Add NaOH to adjust between 5.5-6.5.
10. Add the required NaCl to the batch and leave to mix for 10 minutes.
11. Add encapsulates 200 g of formulation produced according to steps 1-10 produced Formulation A detailed below.

| Component | Trade Name | Supplier | Activity/% | As 100%/% | | |
|---|---|---|---|---|---|---|
| Anionic surfactant SLES 1EO | Texapon N701 | BASF | 28 | 9 | 6 | 3 |
| Glycolipid surfactant at 25%, 50% and 75% of total surfactant | JBR425 Rhamnolipid | Jeneil (JBR 425) | 25 | 3 | 6 | 9 |
| Water | | | 100 | 38.5 | | |
| crosslinked polyacrylate polymer | Carbopol 980 | BF Goodrich | 4 | 0.4 | | |
| Perfume | | | 100 | 0.7 | | |
| Cationic Polymer: Guar Hydroxypropyl Trimonium Chloride | Jaguar C14S | Rhodia | 100 | 0.2 | | |
| Cocamidopropyl betaine (CAPB) | Tergobetaine CK | Goldschmidt | 30 | 1.6 | | |

-continued

| Component | Trade Name | Supplier | Activity/% | As 100%/% |
|---|---|---|---|---|
| Silicone oil Encapsulate | DC7051HS OASIS cap DETB727 | Dow Corning Givaudan | 44 0.3 | 0.75 |
| NaOH | Glydant plus | Lonza | 50 50 | 0.1 0.1 |
| NaCl | | | 99.5 | 0.5, 1, 1.5, 2 |

1. Rheology Measurement Method

A shampoo formulation was produced at bench scale according to the above Protocol. The composition of the formulations varied in that the total surfactant levels had been gradually replaced with varying amounts of microbially derived biosurfactant. The rheological properties were then assessed using an Anton Paar ASC Rheometer at 25° C.

The rheology measurement was performed with the serrated cup and bob geometry. The bob used was the CC27/P2 SN9625 with the serrated cup related to this geometry. Each cup contained between 24 g to 26 g of samples. All the cups were maintained at 25° C. by a Jumbalo F32 thermo bath.

The rheological measurement contains three different steps:

Step 1 shear stress control measurements from 0.01 Pa to 400 Pa.
Step 2 shear rate control measurements from 0.1 $s^{-1}$ to 1200 $s^{-1}$.
Step 3 shear rate control measurements from 1200 $s^{-1}$ to 0.1 $s^{-1}$.

Figure 1:
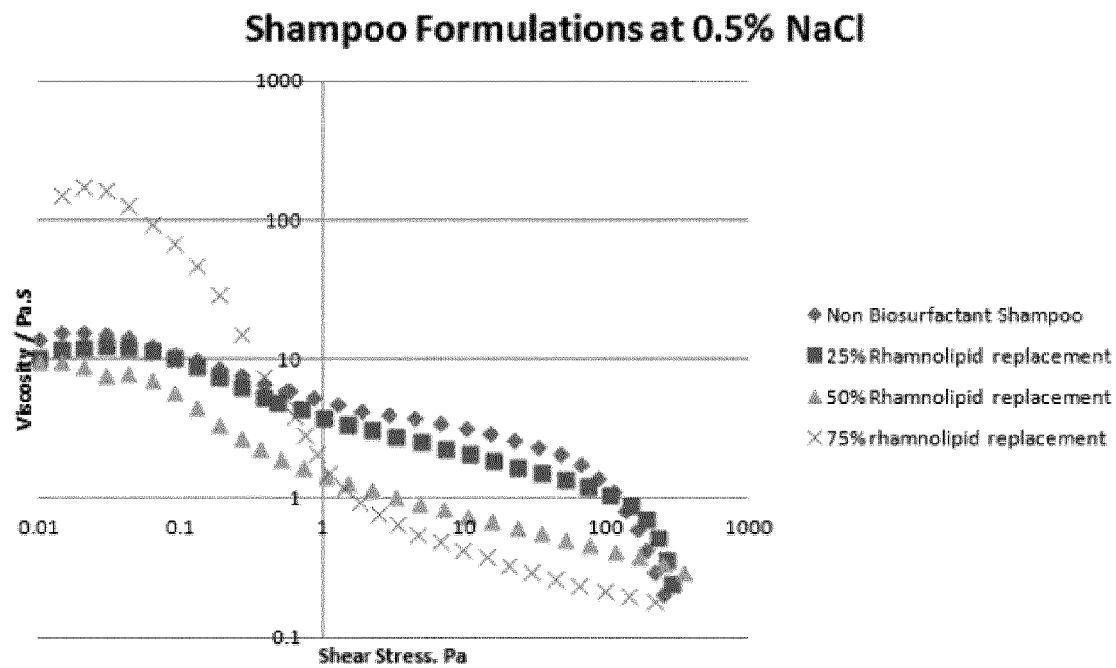
FIG. 1 is a graphical illustration of the rheology profile of Biosurfacant (0%, 25%, 50%, 75%) Shampoo at 0.5% NaCl.
Figure 2:
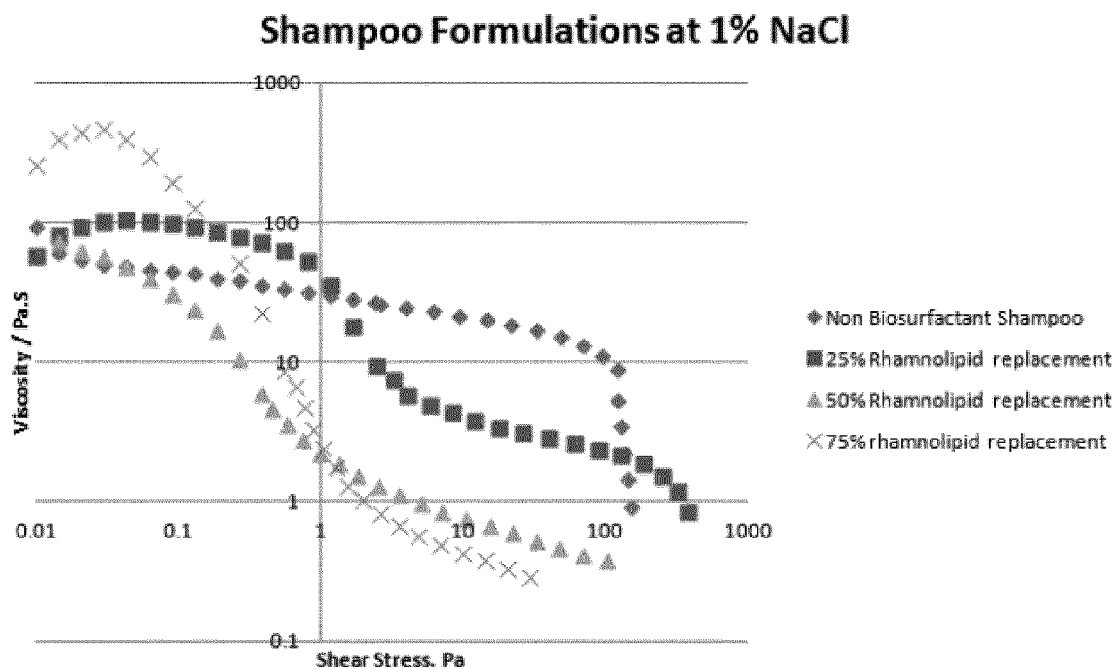
FIG. 2 is a graphical illustration of the rheology profile of Biosurfacant (0%, 25%, 50%, 75%) Shampoo at 1.0% NaCl.
Figure 3:
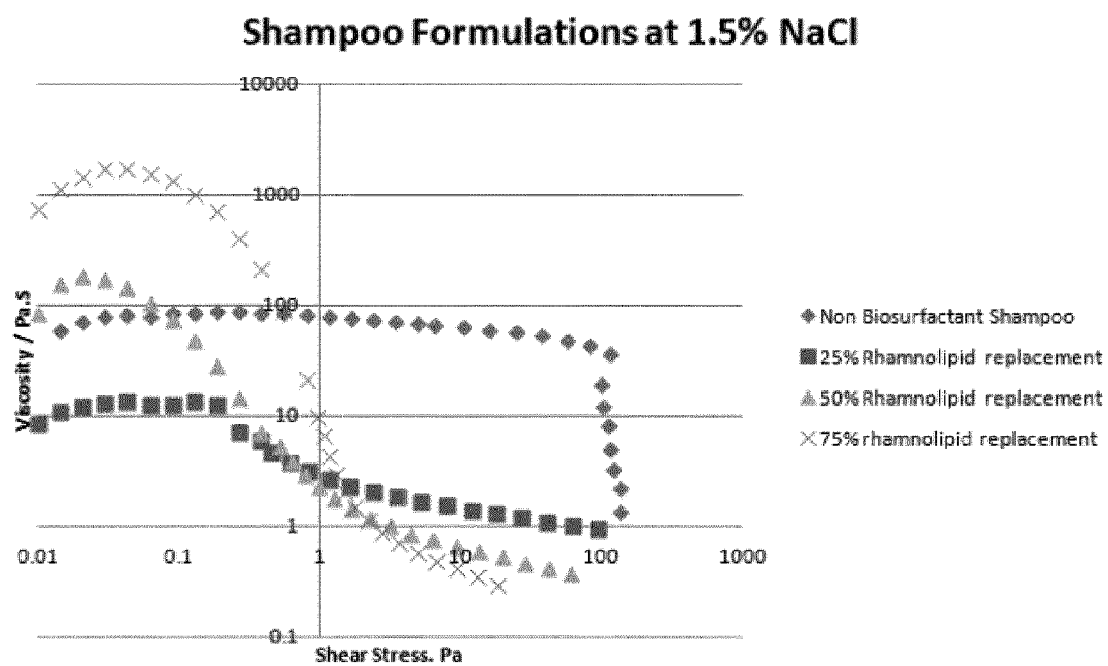
FIG. 3 is a graphical illustration of the rheology profile of is a graphical illustration of the rheology profile of Biosurfacant (0%, 25%, 50%, 75%) Shampoo at 1.5% NaCl.
Figure 4:
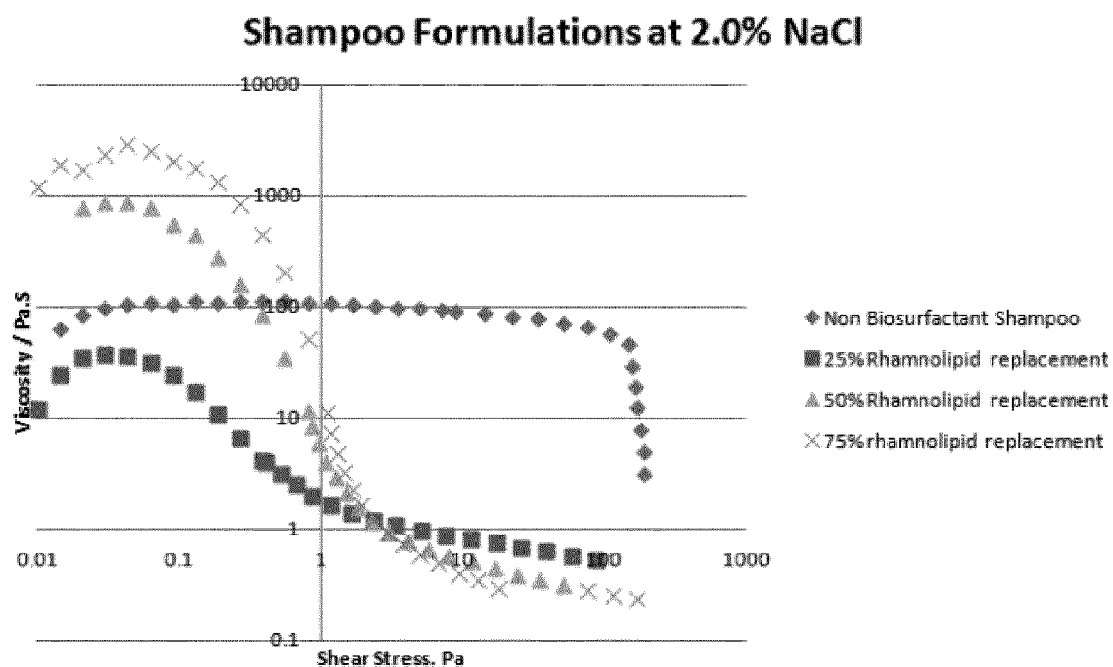
FIG. 4 is a graphical illustration of the rheology profile of a Biosurfacant (0%, 25%, 50%, 75%) Shampoo at 2.0% NaCl.

After the experimental measurement was carried out we collected the data from the Rheoplus software for analysis and this is shown in the following tables 1-5 and also FIGS. 1-4.

TABLE 1

Non-biosurfacant (100% SLES) Shampoo Rheology/varied NaCL

| Shampoo 100% SLES 1EO 0.5% NaCl | | Shampoo 100% SLES 1.0% NaCl | | Shampoo 100% SLES 1.5% NaCl | | Shampoo 100% SLES 2% NaCl | |
|---|---|---|---|---|---|---|---|
| Viscosity | Shear Stress | Viscosity | Shear Stress | Viscosity | Shear Stress | Viscosity | Shear Stress |
| 0.01 | 13.8 | 0.01 | 92.2 | 0.0144 | 60 | 0.0144 | 64 |
| 0.0144 | 15.5 | 0.0144 | 60.4 | 0.0208 | 70.8 | 0.0208 | 83.4 |
| 0.0208 | 15.7 | 0.0208 | 54.6 | 0.0299 | 77.1 | 0.0299 | 96.7 |
| 0.0299 | 15.1 | 0.0299 | 50.2 | 0.0431 | 81.7 | 0.0431 | 103 |
| 0.0431 | 14.3 | 0.0431 | 48.6 | 0.0622 | 79.1 | 0.0622 | 109 |
| 0.0622 | 12.5 | 0.0622 | 45.6 | 0.0896 | 84.9 | 0.0896 | 104 |
| 0.0896 | 10.8 | 0.0896 | 44.1 | 0.129 | 84 | 0.129 | 110 |
| 0.129 | 9.77 | 0.129 | 42.8 | 0.186 | 87.1 | 0.186 | 109 |
| 0.186 | 8.46 | 0.186 | 39.9 | 0.268 | 86 | 0.268 | 113 |
| 0.268 | 7.59 | 0.268 | 38 | 0.386 | 85.4 | 0.386 | 113 |
| 0.386 | 6.68 | 0.386 | 35.8 | 0.557 | 83.5 | 0.557 | 110 |
| 0.557 | 5.99 | 0.557 | 33.7 | 0.802 | 81.2 | 0.802 | 108 |
| 0.586 | 5.86 | 0.802 | 31.8 | 1.16 | 78.9 | 1.16 | 106 |
| 0.859 | 5.24 | 1.16 | 30.1 | 1.67 | 76.4 | 1.67 | 104 |
| 1.26 | 4.68 | 1.67 | 28.3 | 2.4 | 74 | 2.4 | 101 |
| 1.89 | 4.28 | 2.4 | 26.7 | 3.46 | 71.3 | 3.46 | 98.4 |
| 2.91 | 4.02 | 2.61 | 26.1 | 4.99 | 68.8 | 4.99 | 95.3 |
| 4.41 | 3.72 | 4.02 | 24.5 | 6.63 | 66.3 | 7.19 | 92.1 |
| 6.71 | 3.46 | 6.17 | 23 | 10.4 | 63.2 | 8.97 | 89.7 |
| 10.1 | 3.17 | 9.47 | 21.5 | 16.1 | 59.9 | 14.1 | 86 |
| 15.2 | 2.91 | 14.5 | 20 | 24.9 | 56.4 | 22 | 81.8 |
| 22.5 | 2.63 | 21.9 | 18.5 | 38 | 52.6 | 34 | 77.1 |
| 33 | 2.35 | 33 | 17 | 57.1 | 48.2 | 51.7 | 71.6 |
| 47.2 | 2.05 | 48.6 | 15.3 | 82.7 | 42.6 | 76.7 | 64.8 |
| 65.2 | 1.73 | 69.3 | 13.3 | 114 | 35.9 | 110 | 56.4 |
| 86.8 | 1.4 | 94.7 | 11.1 | 101 | 19.3 | 148 | 46.4 |
| 111 | 1.1 | 123 | 8.74 | 104 | 12.1 | 154 | 29.4 |
| 137 | 0.827 | 123 | 5.36 | 113 | 8.04 | 164 | 19.2 |

TABLE 1-continued

Non-biosurfactant (100% SLES) Shampoo Rheology/varied NaCL

| Shampoo 100% SLES 1EO 0.5% NaCl | | Shampoo 100% SLES 1.0% NaCl | | Shampoo 100% SLES 1.5% NaCl | | Shampoo 100% SLES 2% NaCl | |
|---|---|---|---|---|---|---|---|
| Viscosity | Shear Stress | Viscosity | Shear Stress | Viscosity | Shear Stress | Viscosity | Shear Stress |
| 163 | 0.6 | 130 | 3.44 | 115 | 4.99 | 171 | 12.2 |
| 189 | 0.424 | 136 | 2.21 | 120 | 3.18 | 178 | 7.73 |
| 216 | 0.295 | 143 | 1.42 | 136 | 2.2 | 188 | 5 |
| 247 | 0.205 | 150 | 0.905 | 137 | 1.35 | 190 | 3.08 |
|  |  | 158 | 0.581 | 138 | 0.833 | 196 | 1.93 |
|  |  | 163 | 0.365 | 139 | 0.509 | 200 | 1.21 |
|  |  | 161 | 0.22 | 145 | 0.325 | 209 | 0.768 |
|  |  | 171 | 0.143 | 159 | 0.218 | 223 | 0.5 |
|  |  |  |  | 187 | 0.155 | 249 | 0.34 |
|  |  |  |  | 286 | 0.239 |  |  |

TABLE 2

Biosurfacant (25%, 50%75%) Shampoo Rheology at 0.5% NaCl

| 75% SLES1EO-25% JBR 425-0.5% NaCl | | 50% SLES1EO-50% JBR 425-0.5% NaCl | | 25% SLES1EO 75% JBR 0.5% NaCl | |
|---|---|---|---|---|---|
| Viscosity | Shear Stress | Viscosity | Shear Stress | Viscosity | Shear Stress |
| 0.01 | 10.2 | 0.01 | 9.66 | 0.0144 | 151 |
| 0.0144 | 11.6 | 0.0144 | 9.49 | 0.0208 | 171 |
| 0.0208 | 12.2 | 0.0208 | 8.92 | 0.0299 | 162 |
| 0.0299 | 12.4 | 0.0299 | 7.76 | 0.0431 | 126 |
| 0.0431 | 12.1 | 0.0431 | 7.95 | 0.0622 | 92.3 |
| 0.0622 | 11.3 | 0.0622 | 7.03 | 0.0896 | 67.1 |
| 0.0896 | 10.1 | 0.0896 | 5.76 | 0.129 | 47.2 |
| 0.129 | 8.77 | 0.129 | 4.45 | 0.186 | 29.3 |
| 0.186 | 7.45 | 0.186 | 3.36 | 0.268 | 15.1 |
| 0.268 | 6.27 | 0.269 | 2.69 | 0.386 | 7.45 |
| 0.386 | 5.34 | 0.367 | 2.24 | 0.53 | 5.3 |
| 0.485 | 4.85 | 0.507 | 1.89 | 0.633 | 3.86 |
| 0.704 | 4.29 | 0.721 | 1.64 | 0.753 | 2.8 |
| 1.02 | 3.8 | 1.05 | 1.45 | 0.901 | 2.05 |
| 1.5 | 3.4 | 1.51 | 1.27 | 1.1 | 1.53 |
| 2.23 | 3.08 | 2.22 | 1.15 | 1.41 | 1.19 |
| 3.3 | 2.79 | 3.28 | 1.03 | 1.83 | 0.941 |
| 4.9 | 2.52 | 4.83 | 0.926 | 2.45 | 0.77 |
| 7.25 | 2.28 | 7.14 | 0.835 | 3.37 | 0.647 |
| 10.7 | 2.06 | 10.6 | 0.752 | 4.74 | 0.554 |
| 15.9 | 1.86 | 15.6 | 0.679 | 6.77 | 0.483 |
| 23.6 | 1.68 | 23.2 | 0.614 | 9.78 | 0.426 |
| 34.9 | 1.52 | 34.4 | 0.557 | 14.2 | 0.377 |
| 51.2 | 1.36 | 51 | 0.504 | 20.5 | 0.332 |
| 74.4 | 1.2 | 76.2 | 0.459 | 29.6 | 0.292 |
| 106 | 1.05 | 114 | 0.418 | 43.2 | 0.26 |
| 146 | 0.88 | 169 | 0.378 | 64 | 0.235 |
| 191 | 0.702 | 247 | 0.337 | 95.9 | 0.215 |
| 233 | 0.521 | 351 | 0.293 | 145 | 0.198 |
| 262 | 0.357 |  |  | 220 | 0.184 |
| 287 | 0.24 |  |  |  |  |

TABLE 3

Biosurfacant (25%, 50%, 75%) Shampoo Rheology at 1.0% NaCl

| 75% SLES1EO-25% JBR 425-1% NaCl | | 50% SLES1EO 50% JBR 1% NaCl | | 25% SLES1EO-75% JBR 425-1% NaCl | |
|---|---|---|---|---|---|
| Viscosity | Shear Stress | Viscosity | Shear Stress | Viscosity | Shear Stress |
| 0.01 | 57.3 | 0.0144 | 73.9 | 0.01 | 256 |
| 0.0144 | 80.4 | 0.0208 | 63.2 | 0.0144 | 396 |

TABLE 3-continued

Biosurfacant (25%, 50%, 75%) Shampoo Rheology at 1.0% NaCl

| 75% SLES1EO-25% JBR 425-1% NaCl | | 50% SLES1EO 50% JBR 1% NaCl | | 25% SLES1EO-75% JBR 425-1% NaCl | |
|---|---|---|---|---|---|
| Viscosity | Shear Stress | Viscosity | Shear Stress | Viscosity | Shear Stress |
| 0.0208 | 92.4 | 0.0299 | 57.7 | 0.0208 | 443 |
| 0.0299 | 100 | 0.0431 | 48.8 | 0.0299 | 461 |
| 0.0431 | 103 | 0.0622 | 39.8 | 0.0431 | 390 |
| 0.0622 | 102 | 0.0896 | 31.1 | 0.0622 | 293 |
| 0.0896 | 98.2 | 0.129 | 23.5 | 0.0896 | 194 |
| 0.129 | 93.1 | 0.186 | 16.8 | 0.129 | 128 |
| 0.186 | 86.2 | 0.268 | 10.6 | 0.186 | 85.7 |
| 0.268 | 79.2 | 0.386 | 5.88 | 0.268 | 51 |
| 0.386 | 71.1 | 0.456 | 4.56 | 0.386 | 22.2 |
| 0.557 | 62.5 | 0.584 | 3.56 | 0.557 | 8.68 |
| 0.802 | 52.2 | 0.747 | 2.78 | 0.665 | 6.65 |
| 1.16 | 35.1 | 0.982 | 2.23 | 0.769 | 4.69 |
| 1.67 | 17.8 | 1.33 | 1.84 | 0.889 | 3.31 |
| 2.5 | 9.31 | 1.81 | 1.53 | 1.05 | 2.38 |
| 3.24 | 7.35 | 2.52 | 1.3 | 1.25 | 1.73 |
| 4.13 | 5.72 | 3.56 | 1.12 | 1.54 | 1.3 |
| 5.83 | 4.93 | 5.04 | 0.966 | 1.97 | 1.01 |
| 8.34 | 4.3 | 7.2 | 0.842 | 2.59 | 0.814 |
| 12 | 3.78 | 10.5 | 0.747 | 3.5 | 0.671 |
| 17.7 | 3.39 | 15.3 | 0.666 | 4.86 | 0.568 |
| 26.4 | 3.08 | 22.4 | 0.595 | 6.88 | 0.49 |
| 39.9 | 2.84 | 32.4 | 0.524 | 9.87 | 0.429 |
| 59.8 | 2.6 | 47.2 | 0.466 | 14.2 | 0.377 |
| 88.9 | 2.36 | 69.4 | 0.418 | 20.3 | 0.329 |
| 130 | 2.11 | 102 | 0.376 | 29.2 | 0.288 |
| 185 | 1.83 | 185 | 1.83 |  |  |
| 252 | 1.52 | 252 | 1.52 |  |  |
| 321 | 1.18 | 321 | 1.18 |  |  |
| 378 | 0.846 | 378 | 0.846 |  |  |
| 422 | 0.576 | 422 | 0.576 |  |  |
| 459 | 0.383 | 459 | 0.383 |  |  |

TABLE 4

Biosurfacant (25%, 50%, 75%) Shampoo Rheology at 1.5% NaCl

| 75% SLES1EO-25% JBR 425-1.5% NaCl | | 50% SLES1EO 50% JBR 1.5% NaCl | | 25% SLES1EO-75% JBR 425-1.5% NaCl | |
|---|---|---|---|---|---|
| Viscosity | Shear Stress | Viscosity | Shear Stress | Viscosity | Shear Stress |
| 0.01 | 8.37 | 0.01 | 84.8 | 0.01 | 722 |
| 0.0144 | 10.6 | 0.0144 | 152 | 0.0144 | 1,100 |
| 0.0208 | 12.1 | 0.0208 | 180 | 0.0208 | 1,410 |

TABLE 4-continued

Biosurfacant (25%, 50%, 75%) Shampoo Rheology at 1.5% NaCl

| 75% SLES1EO-25% JBR 425-1.5% NaCl | | 50% SLES1EO 50% JBR 1.5% NaCl | | 25% SLES1EO-75% JBR 425-1.5% NaCl | |
|---|---|---|---|---|---|
| Viscosity | Shear Stress | Viscosity | Shear Stress | Viscosity | Shear Stress |
| 0.0299 | 13 | 0.0299 | 172 | 0.0299 | 1,730 |
| 0.0431 | 13.1 | 0.0431 | 142 | 0.0431 | 1,720 |
| 0.0622 | 12.3 | 0.0622 | 105 | 0.0622 | 1,520 |
| 0.0896 | 12.4 | 0.0896 | 71.8 | 0.0896 | 1,320 |
| 0.129 | 13.3 | 0.129 | 47.5 | 0.129 | 1,020 |
| 0.186 | 12.5 | 0.186 | 28.1 | 0.186 | 714 |
| 0.268 | 6.96 | 0.268 | 14.2 | 0.268 | 406 |
| 0.386 | 5.82 | 0.386 | 7.07 | 0.386 | 213 |
| 0.453 | 4.53 | 0.523 | 5.23 | 0.557 | 90.6 |
| 0.612 | 3.74 | 0.64 | 3.9 | 0.802 | 21.1 |
| 0.827 | 3.08 | 0.791 | 2.94 | 0.971 | 9.71 |
| 1.15 | 2.61 | 0.989 | 2.25 | 1.06 | 6.47 |
| 1.65 | 2.29 | 1.26 | 1.74 | 1.16 | 4.32 |
| 2.43 | 2.05 | 1.67 | 1.41 | 1.29 | 2.93 |
| 3.57 | 1.84 | 2.26 | 1.16 | 1.48 | 2.05 |
| 5.26 | 1.65 | 3.14 | 0.985 | 1.78 | 1.5 |
| 7.88 | 1.51 | 4.44 | 0.851 | 2.18 | 1.12 |
| 11.9 | 1.39 | 6.38 | 0.746 | 2.77 | 0.87 |
| 17.9 | 1.28 | 9.29 | 0.662 | 3.63 | 0.697 |
| 27.1 | 1.18 | 13.6 | 0.593 | 4.89 | 0.572 |
| 41.1 | 1.09 | 20 | 0.531 | 6.74 | 0.48 |
| 62.2 | 1.01 | 28.8 | 0.467 | 9.38 | 0.408 |
| 93.4 | 0.922 | 41.7 | 0.412 | 13.1 | 0.346 |
| | | 61.2 | 0.368 | 18.2 | 0.295 |

TABLE 5

Biosurfacant (25%, 50%, 75%) Shampoo Rheology at 2.0% NaCl

| 75% SLES1EO-25% JBR 425-2.0% NaCl | | 50% SLES1EO 50% JBR 2.0% NaCl | | 25% SLES1EO-75% JBR 425-2.0% NaCl | |
|---|---|---|---|---|---|
| Viscosity | Shear Stress | Viscosity | Shear Stress | Viscosity | Shear Stress |
| 0.01 | 11.9 | 0.0208 | 777 | 0.01 | 1,190 |
| 0.0144 | 24.5 | 0.0299 | 858 | 0.0144 | 1,900 |
| 0.0208 | 34.5 | 0.0431 | 857 | 0.0208 | 1,730 |
| 0.0299 | 37.6 | 0.0622 | 788 | 0.0299 | 2,310 |
| 0.0431 | 35.9 | 0.0896 | 550 | 0.0431 | 2,870 |
| 0.0622 | 31.5 | 0.129 | 444 | 0.0622 | 2,500 |
| 0.0896 | 24.6 | 0.186 | 277 | 0.0896 | 2,060 |
| 0.129 | 17 | 0.268 | 159 | 0.129 | 1,750 |
| 0.186 | 10.7 | 0.386 | 83.6 | 0.186 | 1,330 |
| 0.268 | 6.55 | 0.557 | 34.6 | 0.268 | 842 |
| 0.386 | 4.1 | 0.802 | 11.6 | 0.386 | 449 |
| 0.404 | 4.04 | 0.851 | 8.51 | 0.557 | 204 |
| 0.518 | 3.16 | 0.951 | 5.8 | 0.802 | 51.6 |
| 0.666 | 2.48 | 1.08 | 4.03 | 1.1 | 11 |
| 0.87 | 1.97 | 1.27 | 2.88 | 1.18 | 7.2 |
| 1.17 | 1.62 | 1.51 | 2.09 | 1.29 | 4.8 |
| 1.64 | 1.38 | 1.83 | 1.54 | 1.44 | 3.28 |
| 2.33 | 1.2 | 2.26 | 1.17 | 1.66 | 2.29 |
| 3.4 | 1.07 | 2.99 | 0.94 | 1.94 | 1.64 |
| 5.03 | 0.964 | 4.04 | 0.773 | 2.36 | 1.21 |
| 7.52 | 0.879 | 5.62 | 0.657 | 2.94 | 0.925 |
| 11.3 | 0.806 | 8 | 0.57 | 3.79 | 0.725 |
| 17.1 | 0.743 | 11.6 | 0.503 | 5.01 | 0.586 |
| 25.7 | 0.683 | 16.8 | 0.446 | 6.8 | 0.485 |
| 38.7 | 0.627 | 24.1 | 0.391 | 9.35 | 0.406 |
| 58.3 | 0.576 | 35 | 0.345 | 12.9 | 0.341 |
| 87.9 | 0.529 | 51.3 | 0.309 | 17.9 | 0.289 |
| | | | | 76.1 | 0.279 |
| | | | | 114 | 0.255 |
| | | | | 171 | 0.233 |
| | | | | 253 | 0.211 |

2. Suspension: Measurement Method

Composition A as described above and, separately, a control formulation (Formulation A without the glycolipid biosurfactant) were centrifuged at 3700 rpm for using an MSE Centaur II and then the compositions observed for suspension properties.

Results

The encapsulates remain dispersed and suspended in the formulation following 2 hours of centrifuge as above, whereas those of the non-biosurfactant formulation were observed to be clustered, flocculated and sedimented after 15 mins.

The invention claimed is:

1. A fluid cleaning composition comprising:
    (a) a surfactant combination in a fluid comprising:
        (i) a synthetic surfactant; and
        (ii) a glycolipid biosurfactant, wherein the glycolipid biosurfactant is rhamnolipid or sophorolipid, which is present at a level in the range 25-95 wt % of the total surfactant in said surfactant combination, and
    (b) a benefit agent suspended in said fluid, in the absence of additional suspending technology, characterized in that the benefit agent comprises an encapsulate; and
    (c) an ionic salt, wherein the ionic salt comprises halide anions.

2. The fluid cleaning composition according to claim 1 wherein the glycolipid comprises a rhamnolipid.

3. The fluid cleaning composition according to claim 1 wherein the glycolipid biosurfactant is present at 25 wt %-75 wt % of the surfactant combination.

4. The fluid cleaning composition according to claim 1 wherein the benefit agent is greater than or equal to 3 micrometers in diameter.

5. The fluid cleaning composition according to claim 1 wherein the encapsulate comprises a shell or capsule surrounding a core, wherein the core comprises the benefit agent.

6. The fluid cleaning composition according to claim 1 wherein the encapsulate comprises shear/pressure-sensitive action encapsulates, whereby the benefit agent contained within is released in response to mechanical force on the encapsulate.

7. The fluid cleaning composition according to claim 1 wherein the encapsulate comprises urea-formaldehyde and melamine-formaldehyde microcapsules.

8. The fluid cleaning composition according to claim 1 wherein the encapsulate comprises encapsulates of a diffusive action, wherein the benefit agent contained within is also released by diffusion through the outer wall of the encapsulate.

9. The fluid cleaning composition according to claim 1 wherein the encapsulated benefit agent comprises a skin benefit agent or an olfactory benefit agent and/or a volatile benefit agent.

10. The fluid cleaning composition according to claim 1 wherein the encapsulated benefit agent is selected from any one or more or any combination of the following:
    perfumes, insect repellents, essential oils;
    sensates comprising menthol and aromatherapy actives;
    moisturizers and/or emollients for skin and/or hair comprising mineral oil, petrolatum, silicone oil comprising dimethyl polysiloxane, lauryl and myristyl lactate;
    anti-dandruff actives comprising zinc salts selected from the group consisting of zinc pyrithione ZnPTO, zinc sulphate and hydrates thereof; octopirox (piroctone olamine), azole antimicrobials comprising climbazole, selenium sulphide;

silicones comprising polyalkyl siloxanes, polyaryl siloxanes, polyalkylaryl siloxanes, polyether siloxane copolymer, amino silicones, high molecular weight silicone gums and/or crosslinked silicone elastomers; or cationic polymers comprising cationic guar gum or guar hydroxypropyltrimonium chloride.

11. The fluid cleaning composition according to claim 6 wherein the mechanical force is friction, pressure, and/or shear stress.

12. The fluid cleaning composition according to claim 1, wherein the ionic salt is in an amount from 0.01-5 wt %.

13. A fluid cleaning composition comprising:
(a) a surfactant combination in a fluid comprising:
   (i) a synthetic anionic surfactant; and
   (ii) a rhamnolipid biosurfactant, which is present at a level in the range 25-95 wt % of the total surfactant in said surfactant combination, and
(b) a benefit agent suspended in said fluid, in the absence of additional suspending technology, characterized in that the benefit agent comprises an encapsulate; and
(c) an ionic salt, wherein the ionic salt comprises halide anions.

14. The fluid cleaning composition according to claim 13 wherein the rhamnolipid biosurfactant is present at 25 wt %-75 wt % of the surfactant combination.

15. The fluid cleaning composition according to claim 13, wherein the ionic salt is present from 0.01 wt %-5 wt % of the fluid cleaning composition.

16. The fluid cleaning composition according to claim 15, wherein the ionic salt comprises a cation selected from the group consisting of an alkali metal, ammonium, and substituted ammonium cations.

17. The fluid cleaning composition according to claim 15, wherein the ionic salt comprises a metal cation selected from the group consisting of Cs, Na, K, Ca, and Mg cations.

18. The fluid cleaning composition according to claim 13, wherein the surfactant combination is present, at a level of 3 wt %-85 wt %.

19. The fluid cleaning composition according to claim 13, wherein the encapsulated benefit agent is selected from any one or more or any combination of the following:

perfumes, insect repellents, essential oils;

sensates comprising menthol and aromatherapy actives;

moisturizers and/or emollients for skin and/or hair comprising mineral oil, petrolatum, silicone oil comprising dimethyl polysiloxane, lauryl and myristyl lactate;

anti-dandruff actives comprising zinc salts selected from the group consisting of zinc pyrithione ZnPTO, zinc sulphate and hydrates thereof; octopirox (piroctone olamine), azole antimicrobials comprising climbazole, selenium sulphide;

silicones comprising polyalkyl siloxanes, polyaryl siloxanes, polyalkylaryl siloxanes, polyether siloxane copolymer, amino silicones, high molecular weight silicone gums and/or crosslinked silicone elastomers; or cationic polymers comprising cationic guar gum or guar hydroxypropyltrimonium chloride.

20. The fluid cleaning composition according to claim 1, wherein the salt is NaCl.

21. The fluid cleaning composition according to claim 20, wherein the NaCl is present at 0.5-2 wt. %.

22. A fluid cleaning composition comprising:
(a) a surfactant combination in a fluid comprising:
   (i) a synthetic surfactant; and
   (ii) a glycolipid biosurfactant, wherein the glycolipid biosurfactant is rhamnolipid or sophorolipid, which is present at a level in the range 50-95 wt. % of the total surfactant combination, and
(b) a benefit agent suspended in said fluid, in the absence of additional suspending technology, characterized in that the benefit agent comprises an encapsulate
(c) an ionic salt, wherein the ionic salt comprises halide anions.

* * * * *